United States Patent [19]

Jacquet et al.

[11] 4,282,203

[45] Aug. 4, 1981

[54] HAIR LACQUER AND HAIR LOTION COMPOSITIONS CONTAINING A COPOLYMER HAVING UNITS OF A VINYL ALLYL OR METHALLY ESTER OF AN α- OR β-CYCLIC CARBOXYLIC ACID

[75] Inventors: Bernard Jacquet, Antony; Christos Papantoniou, Montmorency; Guy Vanlerberghe, Montjay la Tour; Claude Mahieu, Paris; Vahan Zorayan, Enghien-les-Bains, all of France

[73] Assignee: L'Oreal, Paris, France

[21] Appl. No.: 85,398

[22] Filed: Oct. 16, 1979

[30] Foreign Application Priority Data

Oct. 27, 1978 [FR] France .............................. 78 30596

[51] Int. Cl.³ .............................................. A61K 7/11

[52] U.S. Cl. ...................................... 424/47; 424/70; 424/DIG. 1; 424/DIG. 2

[58] Field of Search ............ 424/DIG. 2, 70, DIG. 1, 424/47

[56] References Cited

U.S. PATENT DOCUMENTS

| 3,684,776 | 8/1972 | Field et al. .................... 424/DIG. 2 |
| 3,981,987 | 9/1976 | Linke et al. .................... 424/DIG. 1 |

*Primary Examiner*—Ethel G. Love
*Attorney, Agent, or Firm*—Cushman, Darby & Cushman

[57] ABSTRACT

A cosmetic composition comprises a cosmetically acceptable vehicle and at least one copolymer having units of a vinyl, allyl or methally ester of an α- or β-cyclic carboxylic acid. A process for producing the said copolymer comprises reacting the monomeric constituents of the copolymer at a temperature between 45°–100° C. for a period ranging from 6 to 24 hours.

15 Claims, No Drawings

HAIR LACQUER AND HAIR LOTION COMPOSITIONS CONTAINING A COPOLYMER HAVING UNITS OF A VINYL ALLYL OR METHALLY ESTER OF AN α- OR β-CYCLIC CARBOXYLIC ACID

The present invention relates to new cosmetic compositions and principally to hair lacquers and hair setting lotions.

BACKGROUND OF THE INVENTION

Among the numerous copolymers used in a conventional manner in the preparation of hair lacquers and hair setting lotions are copolymers of vinyl acetate and crotonic acid, as well as copolymers of vinyl acetate, crotonic acid and a vinyl or allyl ester such as vinyl stearate or allyl stearate.

Attempts over the past years to improve the properties of these copolymers have failed to provide truly significant results with regard to improving their lacquering power and/or the feel or touch of the hair lacquered or set therewith.

In particular, it has not been possible to increase the hardness of these copolymers while at the same time maintaining their other desirable cosmetic properties.

In effect, attempts to improve the hardness characteristics of these copolymers most often has resulted in the production of a copolymer which tended to be brittle. Such brittle copolymers caused the formation of pellicles or powdering which has generally been considered unaesthetic or disadvantageous.

It has now been found that such disadvantages can be overcome or eliminated by using a copolymer exhibiting good lacquering power and providing hair having a pleasant touch when the hair is lacquered or set therewith, the said copolymer having units of a vinyl, allyl or methallyl ester of an α- or β-cyclic carboxylic acid.

DETAILED DESCRIPTION OF THE INVENTION

The present invention relates to a new cosmetic composition and principally to a hair lacquer and hair setting lotion containing as the hair lacquering or hair setting resin an effective amount of at least one copolymer having the following formula I:

$$\left[\begin{array}{c}-CH_2-CH-\\|\\O\\|\\C=O\\|\\CH_3\end{array}\right]_v \left[\begin{array}{c}R\\|\\-CH-CH-\\|\\(Z)_{n-1}\\|\\COOH\end{array}\right]_w \left[\begin{array}{c}R'\\|\\-CH_2-C-\\|\\(CH_2)_{m-1}\\|\\O\\|\\C=O\\|\\(CH_2)_{s-1}\\|\\Cyc\end{array}\right]_x \left[\begin{array}{c}R''\\|\\-CH_2-C-\\|\\(CH_2)_{t-1}\\|\\O\\|\\C=O\\|\\R_1\end{array}\right]_y \quad (I)$$

(Ia)  (Ib)  (Ic)  (Id)

wherein m, n, s and t are 1 or 2,

R, R' and R'' each independently represent hydrogen or methyl,

Z represents a divalent radical selected from the group consisting of $-CH_2-$, $-CH_2-O-CH_2-$ and $-CH_2-O-(CH_2)_2-$, $R_1$ represents linear or branched alkyl or alkenyl, having 2-21 carbon atoms, when s=1, Cyc represents a saturated or unsaturated, mono- or poly-cyclic radical, such as for example, (i) a radical of the formula (ii) a radical of the formula wherein $R_2$ represents hydrogen or methyl and p is 1 or 2, (iii) a radical of the formula and (iv) a radical of the formula wherein $R_3$ represents hydrogen, methyl, ethyl, tert.-butyl, ethoxy, butoxy or dodecoxy and $R_4$ represents hydrogen, alkyl having 1-4 carbon atoms or alkoxy having 1-4 carbon atoms;

when s=2, Cyc represents a radical of the formula wherein $R'_3$ and $R'_4$ have the same meanings given for $R_3$ and $R_4$, respectively, v represents 10-91 and preferably 36-84 weight percent, w represents 3-20 and preferably 6-12 weight percent, x represents 4–60 and preferably 6–40 weight percent, and y represents 0–40 and preferably 2–30 weight percent, with the sum of v+w+x+y being equal to 100 weight percent.

The units of formula (Ib) are derived from the polymerization of an unsaturated carboxylic acid having the formula, R—CH=CH—(Z)$_{n-1}$—COOH (II), wherein R, Z and n have the meanings given above.

Representative unsaturated carboxylic acids usefully employed in the present invention include, crotonic acid, allyloxyacetic acid, allyloxypropionic acid and vinylacetic acid. In accordance with a particular embodiment of the present invention, crotonic acid is preferably employed.

The units of formula (Ic) in the above polymer are derived from the polymerization of a vinyl, allyl or methallyl ester of an α- or β-cyclic carboxylic acid having the following formula:

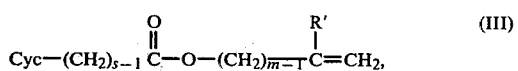

wherein Cyc, R', m and s have the same meanings given above.

Representative esters of this type include, for instance, the vinyl, allyl and methallyl esters of 1-adamantane carboxylic acid, cyclohexane carboxylic acid, cyclopentane carboxylic acid, benzoic acid, phenylacetic acid, 4-tert.-butyl-1-benzoic acid, cyclopentane 1-methyl 1-carboxylic acid, cyclohexane 1-methyl 1-carboxylic acid, tricyclo-[5.2.1.0.$^{2,6}$] decane 3-carboxylic acid and tricyclo-[5.2.1.0.$^{2,6}$] decane 4-carboxylic acid, these latter two acids being sold by Hoechst under the trade name of "TCD Carboxylic Acid S".

As shown by general formula (I) the copolymers of this invention can also have units of formula (Id) which are derived from the polymerization of a vinyl, allyl or methallyl ester having the following formula,

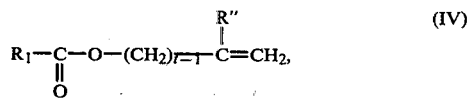

wherein R$_1$, R" and t have the meanings given above.

Representative of esters of this type are the vinyl, allyl and methallyl esters of propionic acid, butyric acid, pivalic acid, hexanoic acid, octanoic acid, decanoic acid, lauric acid, myristic acid, palmitic acid, stearic acid, isostearic acid, behenic acid, 2-ethyl hexanoic acid, 2,2-dimethyl pentanoic acid, 2,2-dimethyl hexanoic acid, 2,2-dimethyl octanoic acid, 2,2-dimethyl decanoic acid, 2,2,4,4-tetramethyl valeric acid, 2-isopropyl-2,3-dimethyl butyric acid, 2-methyl-2-ethyl heptanoic acid, 2-methyl-2-propyl hexanoic acid, 2-methyl-2-isopropyl hexanoic acid, 3,5,5-trimethyl hexanoic acid, and isomers of these acids, as well as mixtures of certain ones of these acids and principally a mixture sold by Shell under the commercial name "Versatique Acide" and mixtures sold by Ugine-Kuhlmann under the commercial name of "Cekanoic C$_8$, C$_9$ and C$_{10}$" acids.

The presence of these esters in the copolymers, principally those having a fatty chain, permit to improve their solubility in the solvents employed for the production of cosmetic compositions and, in particular, those provided in the form of a hair lacquer or hair setting lotion.

Generally, the copolymers of formula (I) have an average molecular weight ranging from 5,000 to 60,000 and, more particularly, between 10,000 and 45,000. These average molecular weights are determined numerically by osometry.

In accordance with the present invention, the cosmetic composition contains from 0.5–10 weight percent of at least one copolymer of formula (I) such as defined above.

The hair setting lotions in accordance with the present invention are provided in the form of an aqueous or hydroalcoholic solution containing from 20 to 70 weight percent alcohol and having a copolymer concentration between, preferably, 1 and 3 weight percent.

The alcohols generally employed for the production of such hair setting lotions are preferably low molecular weight lower aliphatic alcohols such as ethanol or isopropanol.

The aerosol hair lacquer composition, in accordance with the present invention, is obtained by solubilizing in an alcohol at least one copolymer as defined above, this solution being packaged in an aerosol container, pressurized or not.

In accordance with this embodiment of the invention, the copolymer is preferably employed in an amount from 0.7 to 8 weight percent.

The aerosol hair lacquer composition can also contain a third solvent which can be present in an amount from 3 to 35 weight percent.

Representative third solvents include, for instance, methylene chloride, trichloroethane, ethyl chloride, acetone, ethyl acetate and dichlorodifluoroethane.

In the aerosol hair lacquer composition of the present invention, the alcohol which can be either ethanol or isopropanol, is generally present in an amount from 5 to 80 and preferably from 6 to 70 weight percent.

As the aerosol propellant for the aerosol hair lacquer composition there can be employed, fluorochlorinated hydrocarbons either alone, or as a mixture thereof, and principally those known under the commercial names of "Freon" and, in particular, "Freons 11, 12, 22, 133A and 142b".

Other useful propellants include CO$_2$, N$_2$O, dimethylether, hydrocarbons such as propane, butane and isobutane, these propellants being used along or in a mixture thereof or in admixture with one or more "Freons", such as those set forth above.

The composition in accordance with the present invention can also contain various components generally employed in this type of composition such as plasticizers, hair shining agents, perfumes, dyes, hair restructuring agents and anionic, cationic or nonionic surfactants.

In accordance with another embodiment of the present invention, the copolymers of formula (I) such as defined above, can also be employed in compositions in combination with other polymers having an anionic or cationic character, the resulting composition being then in the form of a cream, a gel, an emulsion, a solution or a dispersion.

In accordance with a preferred embodiment of the present invention, the copolymer as defined above is employed in the cosmetic composition in a form neutralized by means of a mineral or organic base selected from the group consisting of NaOH, KOH, ammonia, monoethanolamine, diethanolamine, triethanolamine, isopropanolamine, diisopropanolamine, tri [(2-hydroxy)

1-propyl] amine, 2-amino-2-methyl propanol-1, 2-amino-2-methyl-1,3-propanediol and 2-amino-2-hydroxymethyl-1,3-propanediol, the said neutralization being total or partial.

The present invention also relates to a new copolymer represented by the formula:

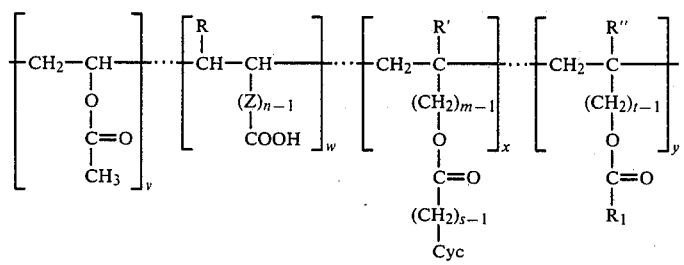

(V)

wherein
m, n, s and t are 1 or 2,
R, R' and R'' represent hydrogen or methyl,
Z represents a divalent radical selected from the group consisting of —CH$_2$—, —CH$_2$—O—CH$_2$— and —CH$_2$—O—(CH$_2$)$_2$—,
R$_1$ represents linear or branched alkyl or alkenyl, having 2-21 carbon atoms,
when s=1, Cyc represents a saturated or unsaturated, mono- or poly-cyclic radical, such as for example,
(i) a radical of the formula

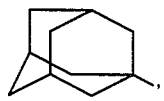

(ii) a radical of the formula

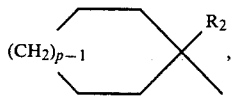

wherein R$_2$ represents hydrogen or methyl, and p is 1 or 2,
(iii) a radical of the formula

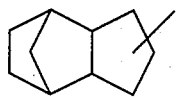

and
(iv) a radical of the formula

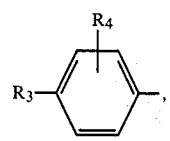

wherein R$_3$ represents hydrogen, methyl, ethyl, tert.-butyl, ethoxy, butoxy or dodecoxy and R$_4$ represents hydrogen, alkyl having 1-4 carbon atoms or alkoxy having 1-4 carbon atoms, with R$_3$ and R$_4$ not simultaneously being hydrogen when m is 1 and R is methyl,
when s=2, Cyc represents a radical of the formula

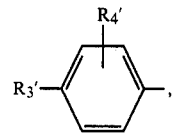

wherein R$'_3$ represents hydrogen, methyl, ethyl, tert.-butyl, ethoxy, butoxy or dodecoxy, and R$'_4$ represents hydrogen, alkyl having 1-4 carbon atoms or alkoxy having 1-4 carbon atoms,
v represents 10-91 and preferably 36-84 weight percent,
w represents 3-20 and preferably 6-12 weight percent,
x represents 4-60 and preferably 6-40 weight percent, and
y represents 0-40 and preferably 2-30 weight percent, with the sum of v+w+x+y being equal to 100 weight percent.

The present invention also relates to a process for preparing the copolymers as defined above.

The copolymers can be obtained by known polymerization methods, i.e. either in solution in a solvent, or in mass, or even in suspension in an inert liquid or in emulsion.

In accordance with a preferred embodiment of the invention, the polymerization reaction is carried out in suspension in water in the presence of a protective colloid or a suspension agent as, for example, polyvinyl alcohol, crosslinked polyacrylic acid or the product known under the trade name "Cellosize WP-09", thereby yielding at the end of the reaction, the polymer in pearl form.

Representative copolymerization initiators include benzoyl peroxide, azobisisobutyronitrile, tert. butyl 2-ethyl perhexanoate, tert.-butyl perpivalate, and, in particular, bis (4-tert.-butyl cyclohexyl)peroxydicarbonate, these initiators being used alone or in admixture.

The amount of initiator is generally between 0.1 and 6 weight percent based on the total weight of the monomers being copolymerized.

The copolymerization reaction is preferably carried out at a temperature between 45° and 100° C., and, more particularly, at the reflux temperature of the reaction mixture.

The reaction time is preferably between 6 and 24 hours.

The following non-limiting examples of preparing the copolymers, as well as examples of cosmetic compositions in the form of hair setting lotions and aerosol hair lacquers are given to better understand the invention.

Unless otherwise stated all parts and percentages are by weight.

EXAMPLES OF PREPARING THE COPOLYMERS

EXAMPLE 1

In a 2 liter flask fitted with an agitator, a condenser and a nitrogen lead-in tube, there are introduced 160 g of vinyl acetate, 20 g of crotonic acid, 20 g of 4-tert.-butyl vinyl benzoate, 3.6 g of bis (4-tert.-butyl cyclohexyl)peroxydicarbonate sold by Akzo under the trade name "Perkadox-16" and 600 g of water containing 1.2% of "Cellosize WP-09". The reaction mixture is then heated for 8 hours at reflux.

At the end of the copolymerization reaction, the residual vinyl acetate is distilled off and the reaction mixture is filtered. The resulting polymer in pearl form is then washed.

After drying the polymer, under reduced pressure, it exhibits an acid index of 64 and a viscosity of 2.77 centipoises in a 5% solution of dimethylformamide at 34.6° C.

Using the same operating methods as described in the above Example, but replacing the 3.6 g of bis (4-tert. butyl cyclohexyl)peroxydicarbonate by 3.4 g of benzoyl peroxide, the copolymers set forth in Tables I and II below have also been prepared.

EXAMPLES OF COSMETIC COMPOSITIONS

EXAMPLE A

An aerosol hair lacquer composition in accordance with the invention is prepared by admixing the following components:

| | |
|---|---|
| Copolymer prepared in Example 1 | 7.6 g |
| 2-amino-2-methyl propanol-1, sufficient for pH = 7 | |
| Ethanol, sufficient for | 100 g |

22 g of the resulting composition are then packaged in an aerosol container together with 78 g of a 61.5:38.5 mixture of Freon 11:Freon 12.

After application of this lacquer onto the hair, it is observed that the hair has an excellent hold as well as a pleasant touch or feel. Further, no production of any copolymer powdering is observed over a prolonged period of time.

EXAMPLE B

A hair lacquer composition of the present invention is prepared by packaging in an aerosol container the following components:

| | |
|---|---|
| Copolymer of Example 4 | 2 g |
| Ethanol | 40 g |
| Methylene chloride | 20 g |
| 2-amino-2-methyl propanol-1, | |

TABLE I

| MONOMERS EX | 2 | 3 | 4 | 5 | 6 | 7 | 8 | 9 | 10 | 11 | 12 |
|---|---|---|---|---|---|---|---|---|---|---|---|
| (1) vinyl acetate | 75 | 80 | 80 | 80 | 80 | 80 | 80 | 70 | 70 | 70 | 70 |
| (2) crotonic acid | 10 | 10 | 10 | 10 | 10 | 10 | 10 | 10 | 10 | 10 | 10 |
| (3) vinyl benzoate | 5 | | | | | | | 10 | | | 10 |
| allyl benzoate | | 10 | | | | | | | 10 | | |
| 4-t.-butyl vinyl benzoate | | | | | | | | | | 10 | |
| vinyl cyclohexane carboxylate | | | 10 | | | | | | | | |
| vinyl cyclopentane carboxylate | | | | 10 | | | | | | | |
| vinyl 1-adamantane carboxylate | | | | | 10 | | | | | | |
| vinyl 1-methyl cyclopentane carboxylate | | | | | | 10 | | | | | |
| vinyl 1-methyl cyclohexane carboxylate | | | | | | | 10 | | | | |
| (4) vinyl stearate | 10 | | | | | | | | | | 10 |
| vinyl versatate | | | | | | | | 10 | 10 | 10 | |
| Acid Index | 64 | 67 | 70 | 66 | 64 | 65 | 67 | 63 | 62 | 62 | 65 |
| Viscosity (in 5% DMF solution at 34.6° C.) | 2.98 | 2.56 | 2.8 | 2.4 | 2.9 | 2.8 | 2.6 | 2.83 | 2.07 | 2.45 | 3.26 |

TABLE II

| MONOMERS EX | 13 | 14 | 15 | 16 | 17 | 18 | 19 | 20 | 21 | 22 | 23 | 24 |
|---|---|---|---|---|---|---|---|---|---|---|---|---|
| (1) vinyl acetate | 70 | 70 | 70 | 70 | 70 | 70 | 65 | 70 | 70 | 72 | 72 | 72 |
| (2) crotonic acid | 10 | 10 | 10 | 10 | 10 | 10 | 10 | 10 | 10 | | | |
| allyloxyacetic acid | | | | | | | | | | 8 | 8 | |
| vinylacetic acid | | | | | | | | | | | | 8 |
| (3) vinyl phenylacetate | | | | | | | | | | 10 | | |
| vinyl 4-t-butyl benzoate | 10 | | | | | | 25 | 10 | | | | |
| allyl 4-t-butyl benzoate | | | | | | | | | | | 10 | 10 |
| vinyl cyclohexane carboxylate | | 10 | | | | | | | | | | |
| vinyl cyclopentane carboxylate | | | 10 | | | | | | | | | |
| vinyl 1-adamantane carboxylate | | | | 10 | | | | | | | | |
| vinyl 1-methyl cyclopentane carboxylate | | | | | 10 | | | | | | | |
| vinyl 1-methyl cyclohexane carboxylate | | | | | | 10 | | | | | | |
| vinyl tricyclo[5.2.1.0.$^{2,6}$]decane-3(4) carboxylate | | | | | | | | | 10 | | | |
| (4) vinyl stearate | 10 | 10 | 10 | 10 | 10 | 10 | | | 10 | | | |
| vinyl versatate | | | | | | | | | | 10 | 10 | 10 |
| allyl stearate | | | | | | | | 10 | | | | |
| Acid Index | 66 | 64 | 63 | 65 | 63 | 62 | 68 | 64 | 65 | 45 | 45 | 53 |
| Viscosity (in a 5% solution of DMF at 34.6° C.) | 2.7 | 2.63 | 2.7 | 2.9 | 2.7 | 2.63 | 2.6 | 2.3 | 3.0 | 2.4 | 2.5 | 2.4 |

| | |
|---|---|
| sufficient for pH = 7 | |
| Propellant: mixture of 35 wt% propane and 65 wt% butane | 40 g |

In this example, the copolymer of Example 4 can advantageously be replaced by an equivalent amount of the copolymer prepared in any one of Examples 5–8 and 14–21.

Example C

A hair setting lotion of the present invention is prepared by admixing the following components:

| | |
|---|---|
| Copolymer of Example 9 | 2 g |
| Ethanol | 45 g |
| Perfume | 0.1 g |
| 2-amino-2-methyl propanediol-1,3, sufficient for pH = 7 | |
| Water, sufficient for | 100 g |

After application of 30 cc of this hair setting lotion onto the hair, the hair is rolled up on hair setting rollers and then dried. It is observed that the hair set has an excellent hold thereby evidencing good lacquer power. Further, the use of this copolymer does not produce any powdering over a prolonged period of time.

In this Example, the copolymer of Example 9 can advantageously be replaced by an equivalent amount of the copolymer prepared in any one of Examples 10 to 13.

Example D

An aerosol hair lacquer composition is prepared by admixing the following components:

| | |
|---|---|
| Copolymer of Example 20 | 3 g |
| Ethanol | 60 g |
| Propellant: mixture of 35 weight percent propane/65 weight percent butane | 37 g |

In this Example the polymer of Example 20 can be replaced by the polymer of Example 21.

Example E

A shampoo composition in accordance with the present invention can be prepared by admixing the following components:

| | |
|---|---|
| Copolymer of Example 1 | 0.4 g |
| Chloride of dimethyl allyl ammonium acrylamide, M.W. = >500,000 | 0.6 g |
| Triethanolamine allyl sulfate, wherein the alkyl moiety is $C_{12}$–$C_{14}$ | 12 g |
| Copradiethanolamide | 3 g |
| Lactic acid, sufficient for, pH = 7.5 | |
| Water, sufficient for | 100 g |

EXAMPLE 5

A hair rinse composition is prepared by admixing the following components:

| | |
|---|---|
| Copolymer of Example 22 | 0.6 g |
| Copolymer known under the trade name "GAFQUAT", described in French patent No. 2,077,143 | 0.6 g |
| Mixture of cetylstearyl alcohol and cetylstearyl alcohol oxyethylenated with 15 moles of ethylene oxide | 5 g |
| Triethanolamine, sufficient for pH = 8.7 | |
| Water, sufficient for | 100 g |

In this Example, the copolymer of Example 22 can be replaced by the same amount of the copolymer prepared in any one of Examples 23, 24 and 1–8.

What is claimed is:

1. A cosmetic composition for treating the hair comprising a cosmetically acceptable vehicle and at least one copolymer having the formula:

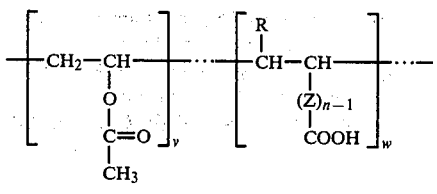

(Ia)  (Ib)

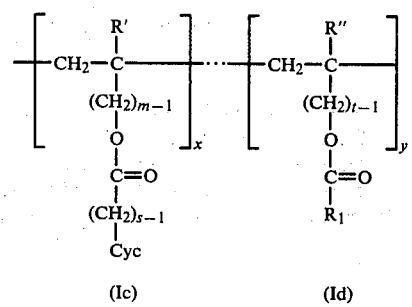

(Ic)  (Id)

wherein:

m, n, s and t are 1 or 2,

R, R' and R" each independently represent hydrogen or methyl,

Z represents a divalent radical selected from the group consisting of —$CH_2$—, —$CH_2$—O—$CH_2$— and —$CH_2$—O—$(CH_2)_2$—, $R_1$ represents linear or branched alkyl or alkenyl, having 2–21 carbon atoms, when s=1, Cyc represents a saturated or unsaturated mono- or poly-cyclic radical selected from the group consisting of:

(i) a radical of the formula

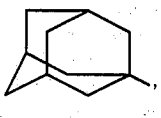

(ii) a radical of the formula

wherein $R_2$ is hydrogen or methyl and p is 1 or 2,
(iii) a radical of the formula

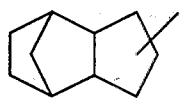

and
(iv) a radical of the formula

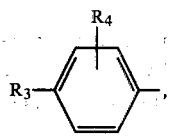

wherein $R_3$ represents hydrogen, methyl, ethyl, tert.-butyl, ethoxy, butoxy or dodecoxy and $R_4$ represents hydrogen, alkyl having 1-4 carbon atoms or alkoxy having 1-4 carbon atoms,
when s=2, Cyc represents a radical of the formula

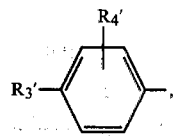

wherein $R'_3$ and $R'_4$ have the same meanings given for $R_3$ and $R_4$, respectively,
v represents from 10 to 91 weight percent,
w represents from 3 to 20 weight percent,
x represents from 4 to 60 weight percent, and
y represents from 0 to 40 weight percent, with the sum v+w+x+y being equal to 100 weight percent.

2. The composition of claim 1 wherein v represents 36 to 84 weight percent, w represents 6 to 12 weight percent, x represents 6 to 40 weight percent and y represents 2 to 30 weight percent.

3. The composition of claim 1 wherein said copolymer is present in an amount of 0.5 to 10 weight percent.

4. The composition of claim 1 wherein said vehicle is water or a hydroalcoholic solution and said copolymer is present in an amount of 1 to 3 weight percent.

5. The composition of claim 1 wherein said vehicle is an alcohol in admixture with a propellant, said composition is packaged in an aerosol container and the said copolymer is present in an amount of 0.7 to 8 weight percent.

6. The composition of claim 5 wherein said alcohol is ethanol or isopropanol.

7. The composition of claim 5 which also includes a third solvent in an amount of 3 to 35 weight percent based on the total weight of the composition.

8. The composition of claim 1 which also includes one or more of a plasticizer, a hair shining agent, a perfume, a dye, a hair restructuring agent or an anionic, cationic or nonionic surfactant.

9. The composition of claim 1 wherein units (Ib) of said copolymer are the residue of an unsaturated carboxylic acid selected from the group consisting of crotonic acid, allyloxyacetic acid, allyloxypropionic acid and vinylacetic acid.

10. The composition of claim 1 wherein units (Ic) of said copolymer are the residue of a vinyl, allyl or methallyl ester of an α- or β-cyclic carboxylic acid selected from the group consisting of 1-adamantane carboxylic acid, cyclohexane carboxylic acid, cyclopentane carboxylic acid, benzoic acid, phenylacetic acid, 4-tert.-butyl-1-benzoic acid, cyclopentane 1-methyl-1-carboxylic acid, cyclohexane 1-methyl 1-carboxylic acid, tricyclo-[5.2.1.0.$^{2,6}$] decane 3-carboxylic acid, tricyclo-[5.2.1.0.$^{2,6}$] decane 4-carboxylic acid and mixtures thereof.

11. The composition of claim 1 wherein units (Id) of said copolymer are the residue of a vinyl, allyl or methallyl ester of an acid selected from the group consisting of propionic acid, butyric acid, pivalic acid, hexanoic acid, octanoic acid, decanoic acid, lauric acid, myristic acid, palmitic acid, stearic acid, isostearic acid, behenic acid, 2-ethyl hexanoic acid, 2,2-dimethyl pentanoic acid, 2,2-dimethyl hexanoic acid, 2,2-dimethyl octanoic acid, 2,2-dimethyl decanoic acid, 2,2,4,4-tetramethyl valeric acid, 2-isopropyl-2,3-dimethyl butyric acid, 2-methyl-2-ethyl heptanoic acid, 2-methyl-2-propyl hexanoic acid, 2-methyl-2-isopropyl hexanoic acid, 3,5,5-trimethyl hexanoic acid, the isomers of said acids and mixtures thereof.

12. A copolymer having the formula

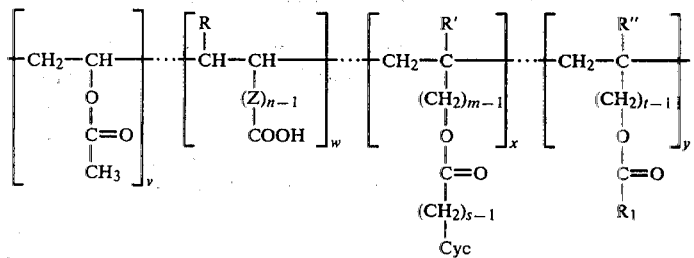

wherein:
m, n, s and t are 1 or 2,
R, R' and R" each independently represent hydrogen or methyl,
Z represents a divalent radical selected from the group consisting of —$CH_2$—, —$CH_2$—O—$CH_2$— and —$CH_2$—O—$(CH_2)_2$,
$R_1$ represents linear or branched alkyl or alkenyl, having 2-21 carbon atoms,
when s=1, Cyc represents a saturated or unsaturated mono- or poly-cyclic radical selected from the group consisting of:

(i) a radical of the formula

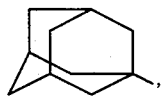, (ii) a radical of the formula

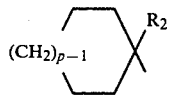

wherein $R_2$ represents hydrogen or methyl and p is 1 or 2, (iii) a radical of the formula

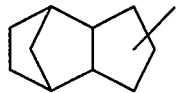

and (iv) a radical of the formula

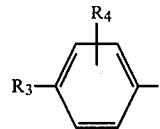

wherein, $R_3$ represents hydrogen, methyl, ethyl, tert.-butyl, ethoxy, butoxy or dodecoxy and $R_4$ represents hydrogen, alkyl having 1-4 carbon atoms or alkoxy having 1-4 carbon atoms, $R_3$ and $R_4$ not simultaneously being hydrogen when m is equal to 1 and when R is methyl, when $s=2$, Cyc represents

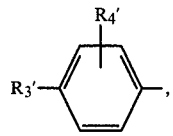, wherein $R'_3$ represents hydrogen, methyl, ethyl, tert.-butyl, ethoxy, butoxy or dodecoxy and $R'_4$ represents hydrogen, alkyl having 1-4 carbon atoms or alkoxy having 1-4 carbon atoms, v represents 10-91 weight percent,
w represents 3-20 weight percent,
x represents 4-60 weight percent, and
y represents 0-40 weight percent, with the sum $v+w+x+y$ being equal to 100 weight percent.

13. The copolymer of claim 12 wherein v represents 36-84 weight percent, w represents 6-12 weight percent, x represents 6-40 weight percent and y represents 2-30 weight percent.

14. The copolymer of claim 12 having an average molecular weight between 5,000 and 60,000, determined by osometry.

15. The copolymer of claim 14 wherein the average molecular weight is between 10,000 and 45,000.

* * * * *